(12) United States Patent
Gordon et al.

(10) Patent No.: US 9,989,480 B2
(45) Date of Patent: Jun. 5, 2018

(54) INSPECTION SYSTEM HAVING AN EXPANDED ANGULAR COVERAGE

(71) Applicant: CAMTEK LTD., Migdal Haemek (IL)

(72) Inventors: Noam Gordon, Haifa (IL); Itay Cohen, Nahariya (IL)

(73) Assignee: CAMTEK LTD., Migdal Haemeq (IL)

( * ) Notice: Subject to any disclaimer, the term of this patent is extended or adjusted under 35 U.S.C. 154(b) by 222 days.

(21) Appl. No.: 15/132,323

(22) Filed: Apr. 19, 2016

(65) Prior Publication Data

US 2016/0313258 A1 Oct. 27, 2016

Related U.S. Application Data

(60) Provisional application No. 62/150,310, filed on Apr. 21, 2015.

(51) Int. Cl.
| | |
|---|---|
| *G01N 21/95* | (2006.01) |
| *H04N 5/225* | (2006.01) |
| *H04N 5/369* | (2011.01) |
| *G02B 19/00* | (2006.01) |

(52) U.S. Cl.
CPC ..... *G01N 21/9515* (2013.01); *G02B 19/0023* (2013.01); *G02B 19/0028* (2013.01); *G02B 19/0047* (2013.01); *H04N 5/2254* (2013.01); *H04N 5/2256* (2013.01); *H04N 5/3692* (2013.01); *G01N 2201/0636* (2013.01); *G01N 2201/0638* (2013.01)

(58) Field of Classification Search
CPC ............ G01N 21/9515; H04N 5/2254; H04N 5/2256; G02B 17/0816; G02B 17/0832; G02B 27/09; G02B 19/0047
See application file for complete search history.

(56) References Cited

U.S. PATENT DOCUMENTS

| 2016/0005588 A1* | 1/2016 | Park ................... G02B 27/141 313/231.31 |
| 2016/0088213 A1* | 3/2016 | Miyai ................. H04N 5/2256 348/349 |

FOREIGN PATENT DOCUMENTS

WO    WO 2007023487 A2 *  3/2007 ......... G01N 21/8806

* cited by examiner

*Primary Examiner* — Behrooz Senfi
(74) *Attorney, Agent, or Firm* — Reches Patents

(57) ABSTRACT

An inspection system having an expanded angular coverage, the inspection system may include a line camera; a first curved mirror; a second curved mirror; a first focusing lens that is positioned between the first mirror and an object; a second focusing lens that is positioned between the second mirror and the object; a first light source that is configured to direct a first part of a first light beam towards the first curved mirror and a second part of the first light beam towards the first focusing lens; a second light source that is configured to direct a first part of a second light beam towards the second curved mirror and a second part of the second light beam towards the second focusing lens.

20 Claims, 7 Drawing Sheets

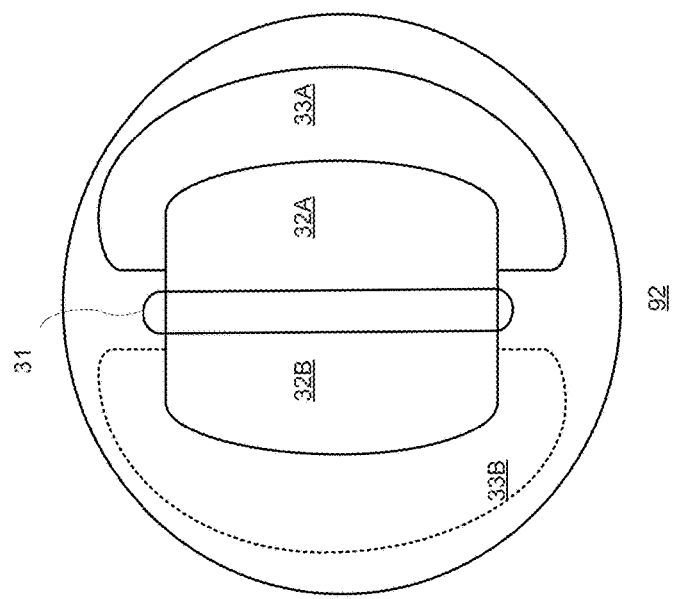
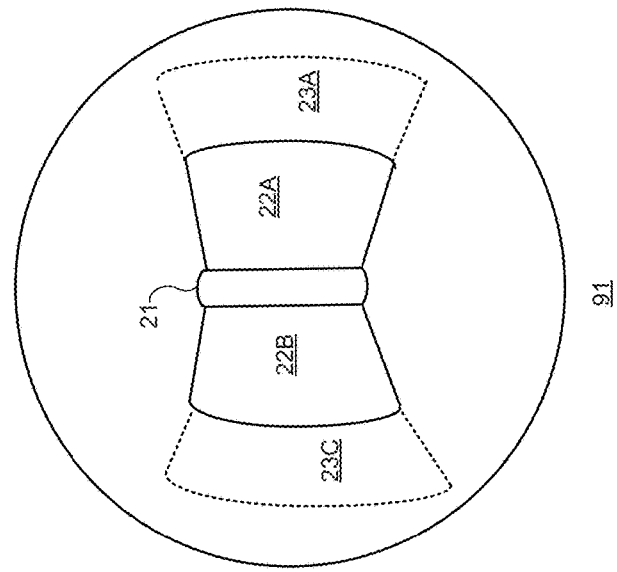
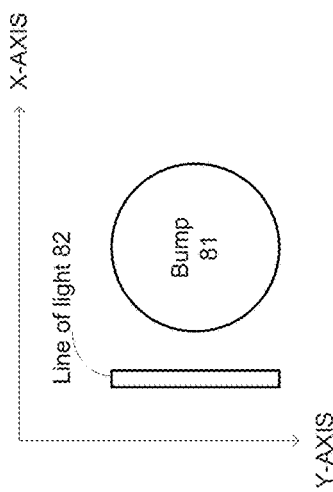
FIG. 3

INSPECTION SYSTEM HAVING AN EXPANDED ANGULAR COVERAGE

BACKGROUND OF THE INVENTION

This application claims priority from U.S. provisional patent Ser. No. 62/150,310 filing date Apr. 21, 2015, which is incorporated herein by reference.

RELATED APPLICATIONS

Inspection and metrology systems require adequate illumination of the inspected article.

There is a growing need to obtain an expanded angular coverage of the illumination, i.e. that incident light from the illuminated article can be reflected and gathered by the imaging system, from a large range of surface angles as well as diffusive and rough surfaces. A particularly important example is printed circuit board (PCB) layers or other electrical circuits such as wafers, whose copper signal lines have a trapezoid-like profile, or having other three dimensional (3D) features such as bumps and dimples.

Current illumination optics arrangements and setups do not achieve satisfactory angular coverage for such steep slopes of trapezoid-like profiles and 3D features. Thus, there is a particularly important need for this invention to achieve the most expanded angular coverage, in order to provide better illumination of such non-flat features.

SUMMARY

According to an embodiment of the invention there may be provided an inspection system having an expanded angular coverage, the inspection system may include a line camera; a first curved mirror; a second curved mirror; a first focusing lens that is positioned between the first mirror and an object; a second focusing lens that is positioned between the second mirror and the object; a first light source that is configured to direct a first part of a first light beam towards the first curved mirror and a second part of the first light beam towards the first focusing lens; a second light source that is configured to direct a first part of a second light beam towards the second curved mirror and a second part of the second light beam towards the second focusing lens; wherein the first curved mirror is configured to reflect the first part of the first light beam to impinge on an area of the object along a first angular range; wherein the second curved mirror is configured to reflect the first part of the second light beam to impinge on the area of the object along a second angular range; wherein the first focusing lens is configured to focus the second part of the first light beam to impinge on the area of the object along a third angular range; wherein the second focusing lens is configured to focus the second part of the second light beam to impinge on the area of the object along a fourth angular range; wherein the first angular range, the second angular range, the third angular range and the fourth angular range differ from each other; and wherein the camera is configured to detect collected light that is within a field of view of the camera and is reflected from the area of the object.

The area of the object may have an elongated shape and may be parallel to the field of view of the camera.

The first light source may be followed by a first beam expander for expanding the first light beam along a plane that may be substantially parallel to a longitudinal axis of the field of view of the camera.

The first light source may be followed by a first beam shaper for controlling the first and third angular ranges.

There may be no angular gap between the first angular range and the third angular range.

There may be no angular gap between the second angular range and the fourth angular range.

The camera has an optical axis; wherein the first and third angular ranges may be positioned at one side of the optical axis and wherein the second and fourth angular ranges may be positioned at another side of the optical axis.

There may be a gap between the first curved mirror and the second curved mirror; and wherein the camera may be configured to detect light that passes through the gap.

The inspection system may include a third curved mirror, a beam splitter and a third light source; wherein the third light source may be configured to direct a third light beam towards the third curved mirror; wherein the third curved mirror may be configured to reflect the third light beam towards the beam splitter; wherein the beam splitter may be configured to direct the third light beam through the gap and towards the area of the object along a fifth angular range.

The first and second curved mirrors may be elliptical or spherical mirrors; wherein the first and second mirrors may be Fresnel mirrors or cylindrical mirrors; and wherein the first and second light sources may be dark field light sources.

According to an embodiment of the invention there may be provided a method for inspecting an object, the method may include illuminating a first curved mirror by a first part of a first light beam; illuminating a first focusing lens by a second part of the first light beam; illuminating a second curved mirror by a first part of a second light beam; illuminating a second focusing lens by a second part of the second light beam; reflecting, by the first curved mirror, the first part of the first light beam to impinge on an area of the object along a first angular range; reflecting, by the second curved mirror, the first part of the second light beam to impinge on an area of the object along a second angular range; focusing, by the first focusing lens, the second part of the first light beam to impinge on the area of the object along a third angular range; focusing, by the second focusing lens, the second part of the second light beam to impinge on the area of the object along a fourth angular range; wherein the first angular range, the second angular range, the third angular range and the fourth angular range differ from each other; and detecting, by a camera, collected light that may be within a field of view of the camera and may be reflected from the area of the object.

The area of the object has an elongated shape and may be parallel to the field of view of the camera.

The method may include expanding the first light beam along a plane that may be substantially parallel to a longitudinal axis of the field of view of the camera.

The method may include shaping the first light beam for controlling the first and third angular ranges.

There may be no angular gap between the first angular range and the third angular range.

There may be no angular gap between the second angular range and the fourth angular range.

The camera has an optical axis; wherein the first and third angular ranges may be positioned at one side of the optical axis and wherein the second and fourth angular ranges may be positioned at another side of the optical axis.

There may be a gap between the first curved mirror and the second curved mirror; and wherein the collected light passes through the gap.

The method may include illuminating a third curved mirror with a third light beam; reflecting, by the third curved mirror, the third light beam towards the beam splitter; directing, by the beam splitter, the third light beam through the gap to impinge on the area of the object along a fifth angular range.

The first and second curved mirrors may be elliptical or spherical mirrors; wherein the first and second focusing mirrors may be Fresnel mirrors or cylindrical mirrors; and wherein the first and second light sources may be dark field light sources.

BRIEF DESCRIPTION OF THE INVENTION

The present invention will be understood and appreciated more fully from the following detailed description taken in conjunction with the drawings in which:

FIG. 3 illustrates a portion of the inspection system of FIG. 1 according to an embodiment of the invention;

DETAILED DESCRIPTION OF THE INVENTION

Figure 1:
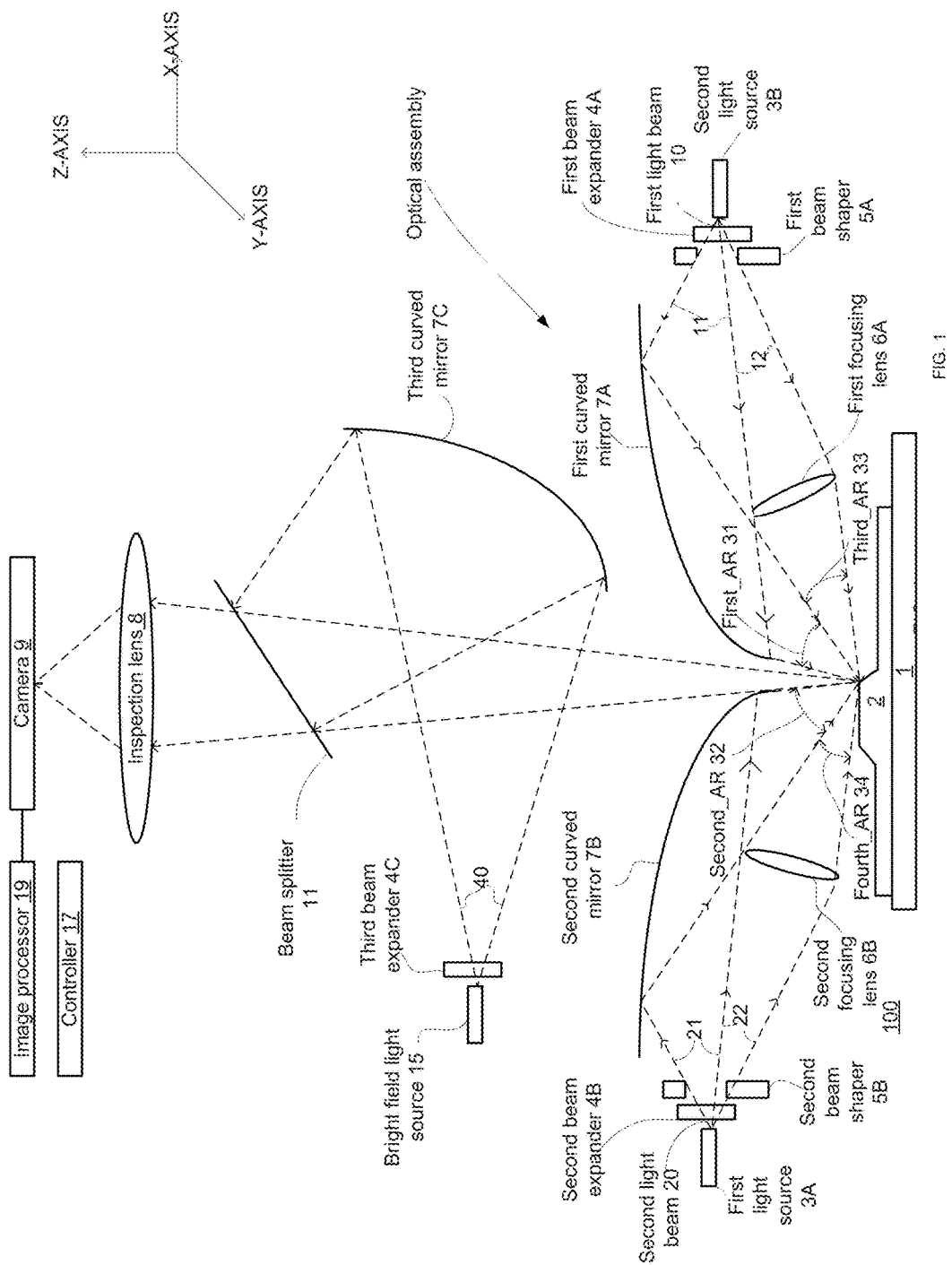
FIG. 1 illustrates an inspection system according to an embodiment of the invention.

Because the apparatus implementing the present invention is, for the most part, composed of electronic components and circuits known to those skilled in the art, circuit details will not be explained in any greater extent than that considered necessary as illustrated above, for the understanding and appreciation of the underlying concepts of the present invention and in order not to obfuscate or distract from the teachings of the present invention.

In the following specification, the invention will be described with reference to specific examples of embodiments of the invention. It will, however, be evident that various modifications and changes may be made therein without departing from the broader spirit and scope of the invention as set forth in the appended claims.

A dark field light source is a light source that illuminates an object with an illuminating light beam that has an illuminating beam optical axis. The illuminating beam optical axis differs from a camera optical axis of a camera that images the object. The illuminating beam optical axis and the camera optical axis are not symmetrical in relation to a normal to the object.

A bright field light source is a light source that illuminates an object with an illuminating light beam that has an illuminating beam optical axis. The illuminating beam optical axis may equal the camera optical axis. Alternatively—the illuminating beam optical axis and the camera optical axis may differ from each other by are symmetrical in relation to a normal to the object.

In the following text there is a reference to first and second parts of a first light beam. The first and second parts of the first light beam are equivalent to two different light beams.

In the following text there is a reference to first and second parts of a second light beam. The first and second parts of the second light beam are equivalent to two different light beams.

The inspection system obtains an expanded angular coverage while using fewer light sources than prior art systems.

Some line-illumination systems known in the art utilize elliptical, spherical, or other mirrored surfaces to focus the illuminated light on the inspected article.

The proposed inspection system extends the attainable angular coverage of such inspection systems by using optical assemblies such as one or more focusing lenses (cylindrical lenses and/or one or more Fresnel lenses) that are positioned in the illumination path and extend the angular coverage—by directing light beams which are not utilized through the optical assembly towards the inspected element. The light beams which were not utilized in prior art inspection system did not illuminate the object or would illuminate the object at a manner that was not caught by the camera.

The optical assembly of the inspection system may include a beam shaper such as but not limited to a shutter or a light blocker for controlling the angular coverage of the illuminating beam.

The beam shaper may have an adjustable transparency (for example may be an LCD screen) and/or may be moved either manually or automatically in accordance to the application or required angular coverage of illumination. The manual or automatic moving of the beam shaper can be controlled using feedback from an image processor (denoted 17 in FIG. 1) which analyses the resulting image. This controls the expansion of the tangential angular coverage.

The inspection system includes an optical assembly that may form additional illumination paths, which collect light from the illumination sources and focus it on the inspected element at steep angles that would otherwise not be covered without the optical assemblies. Thus, the effective angular coverage is greatly improved.

The optical assembly may be calibrated and aligned in order to obtain the optimal tangential angular coverage with uniform elongated light and angular distribution.

In order to extend a sagittal angular coverage (within a plane that extends from the plane of FIG. 1—for example within a Y-Z plane), a Fresnel beam splitter or micro prism array (4A and 4B) with side mirrors may be used.

FIG. 1 illustrates inspection system 100 that includes:
a. A mechanical element such as table 1 for supporting object 2.
b. First and second light sources such as dark-field light sources 3A and 3B.
c. First, second and third beam expanders such as Fresnel beam splitters or micro prism arrays 4A, 4B and 4C. These beam expanders expand the bright-field and dark-field angular coverage within the Y-Z plane.
d. First and second beam shapers such as covers or light blocker 5A and 5B.
e. First and second focusing lenses such as cylinder or Fresnel lens 6A and 6B.
f. First, second and third curved mirrors such as elliptical or spherical mirrors 7A, 7B and 7C.
g. Inspection Lens 8.
h. Camera 9.
i. Third light source such as bright-field light source 15.
j. Beam splitter 11.

Optical assembly 90 may include at least some of the following optical components: first, second and third beam expanders, first, second and third curved mirrors, first and second beam shapers, first and second focusing lenses, first, second and third light sources. It is noted that the bright field light source may also be followed by a beam shaper.

Right dark-field light source 3a is followed by a Fresnel beam splitter or micro prism array 4a that is followed by light blocker 5A. Light (first light beam 10) from dark-field light source 3A passes through Fresnel beam splitter or micro prism array 4A, through the aperture formed by light blocker 5A. A first part (11) of the first light beam is directed towards the right elliptical or spherical mirror 7A ((Ref. WO 2007/023487) and is directed towards object 2. A second part (12) of the first light beam passes through Cylinder or Fresnel lens 6A and is also directed towards object 2.

A left dark-field light source 3B is followed by a Fresnel beam splitter or micro prism array 4B that is followed by light blocker 5B. Light (second light beam 20) from dark-field light source 3B passes through Fresnel beam splitter or micro prism array 4B, through the aperture formed by light blocker 5B. A first part (21) of the light is directed towards the right elliptical or spherical mirror 7B and is directed towards object 2. A second part (22) of the second light beam passes through Cylinder or Fresnel lens 6B and is also directed towards object 2.

Light from bright-field light source 15 passes through Fresnel beam splitter or micro prism array 4C, propagates towards upper elliptical or spherical mirror 7C, is directed toward beam splitter 11 and is directed to pass through a space (gap) between right and left elliptical or spherical mirrors 7A and 7B and to impinge on the erect element of object 2.

Light from the erect element passes through the a space between right and left elliptical or spherical mirrors 7A and 7B, passes through beam splitter 11 and inspection lens 8 and impinges on camera 9.

Right and left cylinder or Fresnel lenses 6A and 6B collect light rays that were not directed towards the erect element, and illuminate the erect element via "lower" angles that were not covered at the absence of right and left cylinder or Fresnel lenses 6A and 6B.

In addition, the Fresnel beam splitter or micro prism arrays in 4A, 4B and 4C can be replaced by or combined with one or more Fresnel beam splitters or micro prism arrays having different optical properties, or repositioned, such that different angular coverage properties will be attained, as required by the application. This change of configuration can be performed manually or automatically by the system.

Figure 2:
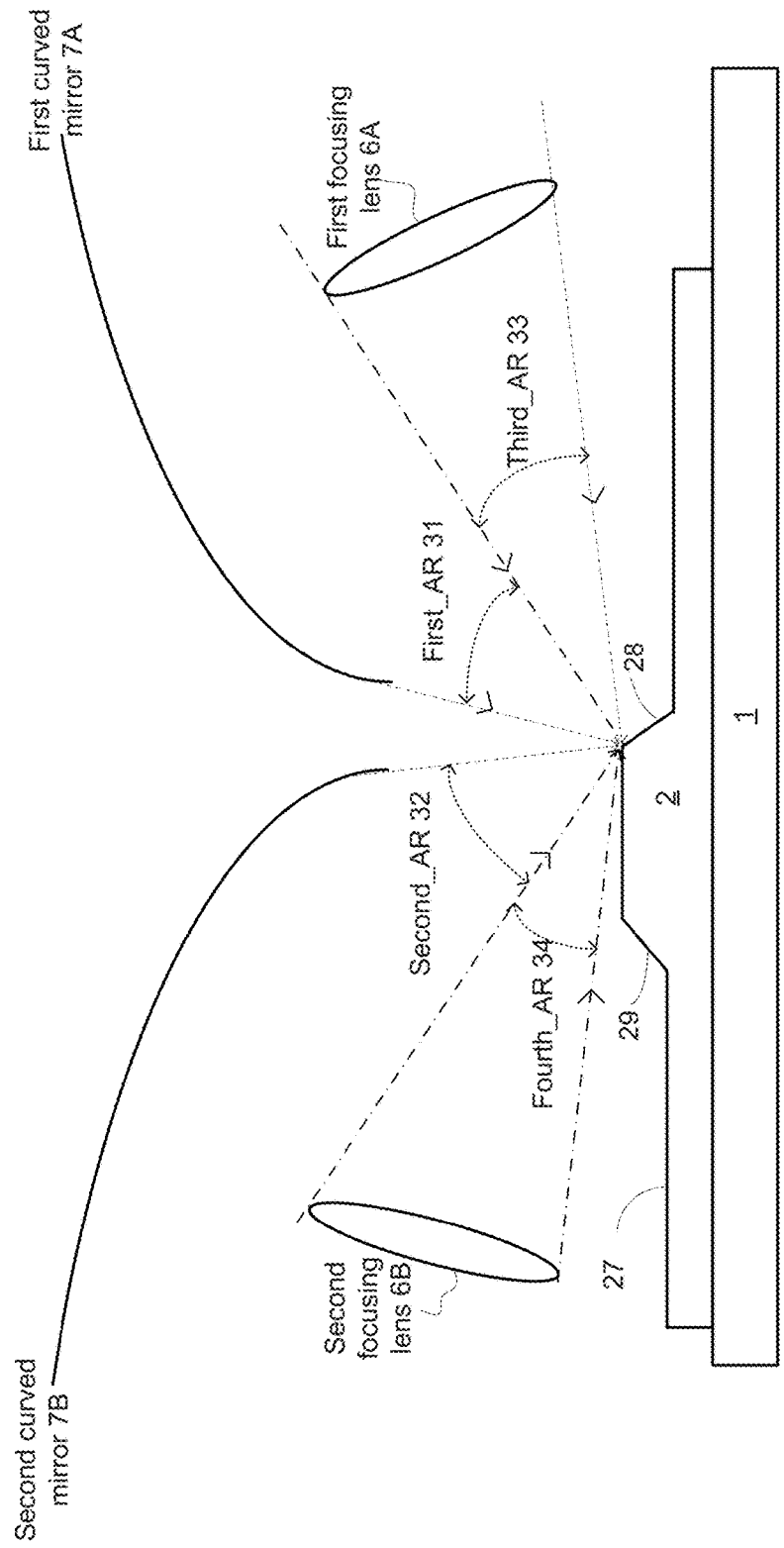
FIG. 2 illustrates a portion of the inspection system of FIG. 1 according to an embodiment of the invention.

FIG. 1 and FIG. 2 also illustrate that:
a. The first part 11 of the first light beam impinges on an area of the object along first angular range First_AR 31.
b. The first part 21 of the second light beam impinges on the area of the object along second angular range Second_AR 32.
c. The second part 12 of the first light beam impinges on the area of the object along third angular range Third_AR 33.
d. The second part 22 of the second light beam impinges the area of the object along second angular range Fourth_AR 34. The fourth angular range may expand, for example, between 54 and 87 degrees.

The first and second angular ranges may expand, for example, between 8 and 54 degrees, between a subset of said range or between a ranges that is substantially identical (for example up to 10% of deviation) from said range.

The third and fourth angular ranges may expand, for example, between 54 and 87 degrees, between a subset of said range or between a ranges that is substantially identical (for example up to 10% of deviation) from said range.

In FIGS. 1 and 2 the first and third angular ranges may form a continuous angular range to the right of the object while the second and fourth angular ranges may form a continuous angular range to the left of the object.

There may be a gap between the first and third angular ranges and/or between the second and fourth angular ranges.

In FIGS. 1 and 2 the system is illustrated as illuminating an edge of object and the light that is collected by the camera 9 may result from the illumination of the object 2 with the second part 12 of the first light beam. When illuminating parts of the object that are oriented at other angles—light resulting from the illuminating of the object by the third light beam, from the second light beam and/or the first part of the first light beam may be collected by the camera 9.

For example—and referring to FIG. 2—horizontal surface 27 will reflect towards camera 9 the bright field light beam. Sloped surface 29 will reflect towards camera 9 the first and/or second parts of the second light beam (depending upon the slope of sloped surface 29). Sloped surface 28 will reflect towards camera 9 the first and/or second parts of the first light beam (depending upon the slope of sloped surface 28).

FIG. 3 illustrates the coverage areas obtained when scanning a metallic dome with and without the Fresnel beam splitter or micro prism arrays (4A, 4B and 4C) according to an embodiment of the invention.

In FIG. 3 the angular coverage represents the light that is generated by a certain light source that once illuminates the dome is collected by camera 9.

The metallic dome (bump 81) is located within a Y-X plane and is scanned along the X-axis with a line of light 82 that is parallel to the X axis.

Image 91 illustrates the coverage areas obtained without the Fresnel beam splitter or micro prism arrays (4A, 4B and 4C).

In image 91:
a. The angular coverage of the bright-field light is represented by region 21.
b. The angular coverage obtained by the first part of the first light beam (from dark field light source 3A) is represented by region 22A.
c. The angular coverage obtained by the first part of the second light beam (from dark field light source 3B) is represented by region 22B.
d. The angular coverage obtained by the second part of the first light beam (from dark field light source 3A) is represented by region 23A.
e. The angular coverage obtained by the second part of the second light beam (from dark field light source 3B) is represented by region 23B.

Image 92 illustrates the coverage areas obtained with the Fresnel beam splitter or micro prism arrays (4A, 4B and 4C).

In image 91:
a. The angular coverage of the bright-field light is represented by region 23.
b. The angular coverage obtained by the first part of the first light beam (from dark field light source 3A) is represented by region 32A.
c. The angular coverage obtained by the first part of the second light beam (from dark field light source 3B) is represented by region 32B.
d. The angular coverage obtained by the second part of the first light beam (from dark field light source 3A) is represented by region 33A.
e. The angular coverage obtained by the second part of the second light beam (from dark field light source 3B) is represented by region 33B.

The usage of the Fresnel beam splitter or micro prism arrays (4A, 4B and 4C) expands the angular coverage along the Y-axis.

Clearly, in accordance with current invention, both tangential (along the X-axis) and sagittal (along the Y-axis) angular coverages are improved significantly.

Figure 4:
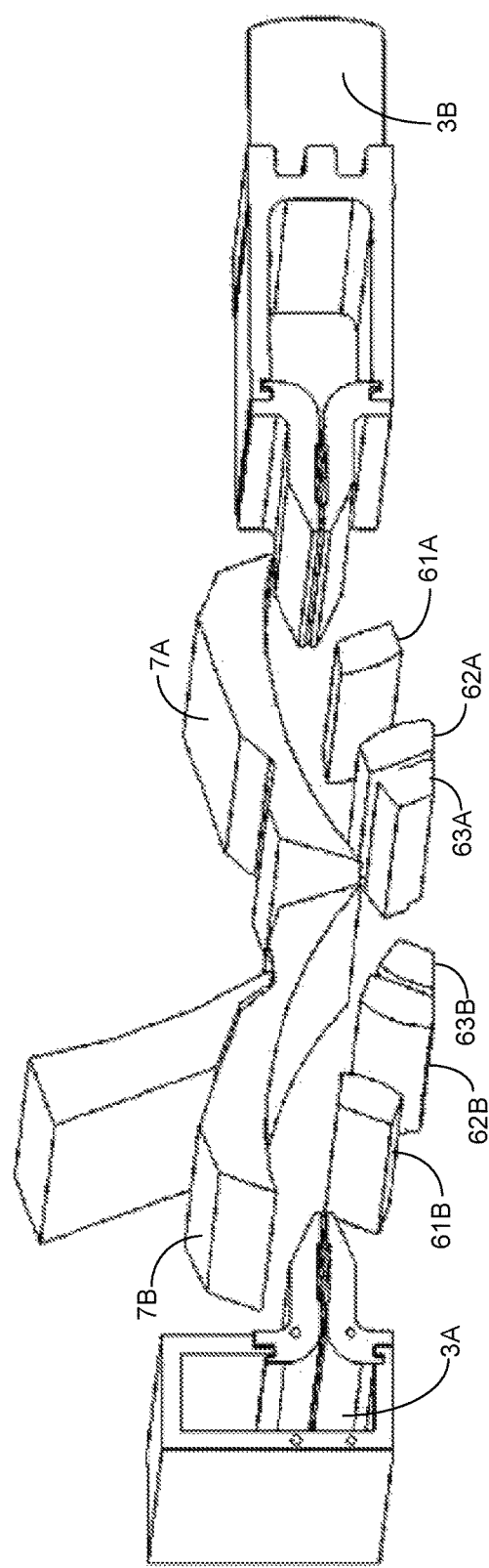
FIG. 4 illustrates a portion of the inspection system of FIG. 1 according to an embodiment of the invention.
Figure 5:
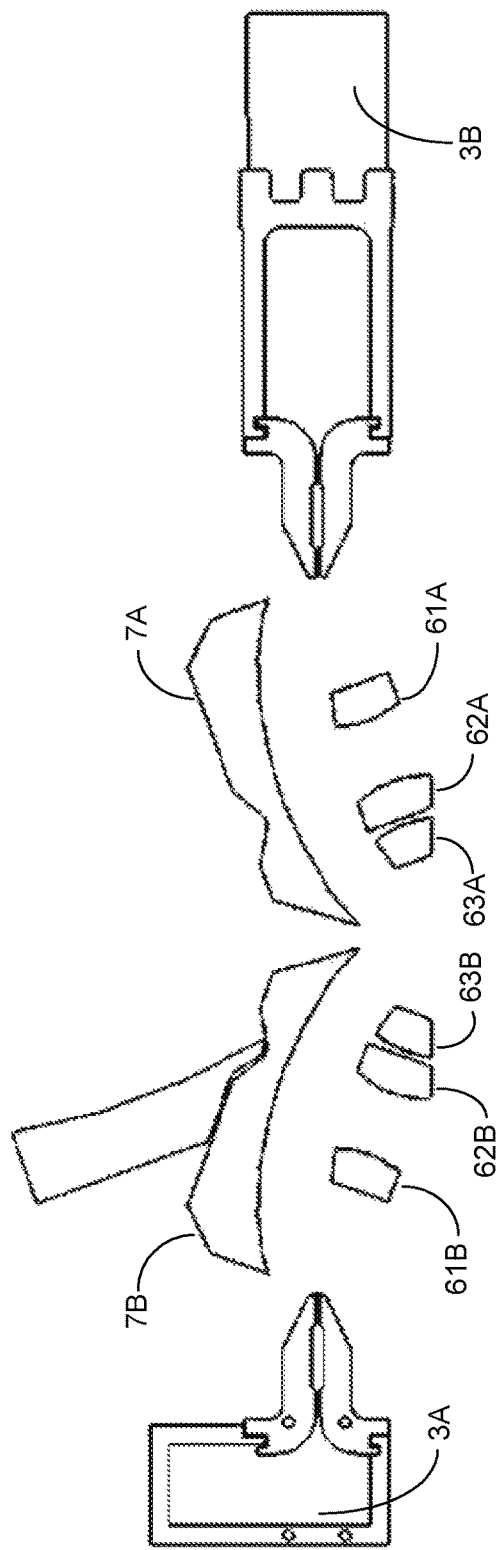
FIG. 5 illustrates a portion of the inspection system of FIG. 1 according to an embodiment of the invention.

FIGS. 4 and 5 illustrate a part of inspection system 100 according to an embodiment of the invention.

These figures illustrates first and second dark field light sources (fibers) 3A and 3B, first and second elliptical or spherical mirrors 7A and 7B. These figures also illustrates each one of first and second cylinder or Fresnel lens 6A and 6B as being formed of three spaced apart lenses—lenses 61A, 62A and 63A form lens 6A, and lenses 61B, 62B and 63B form lens 6B.

Figure 6:
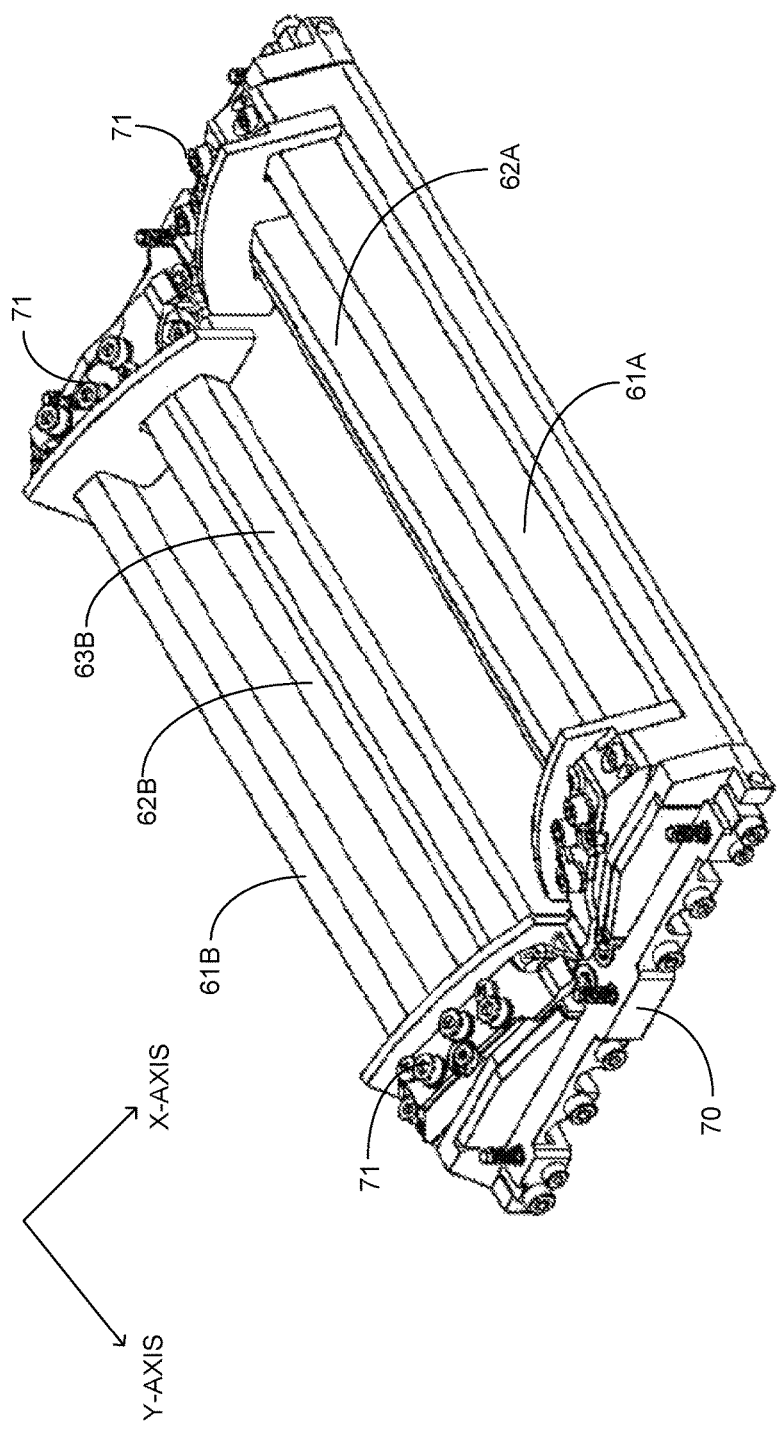
FIG. 6 illustrates coverage areas obtained when illuminating a dome according to various embodiments of the invention.

FIG. 6 illustrates lenses 61A, 62A, 63A, 61B, 62B and 63B and their support and alignment structure according to an embodiment of the invention.

The support and alignment structure includes a frame 70 and multiple securing and alignment elements such as screws 71.

Figure 7:
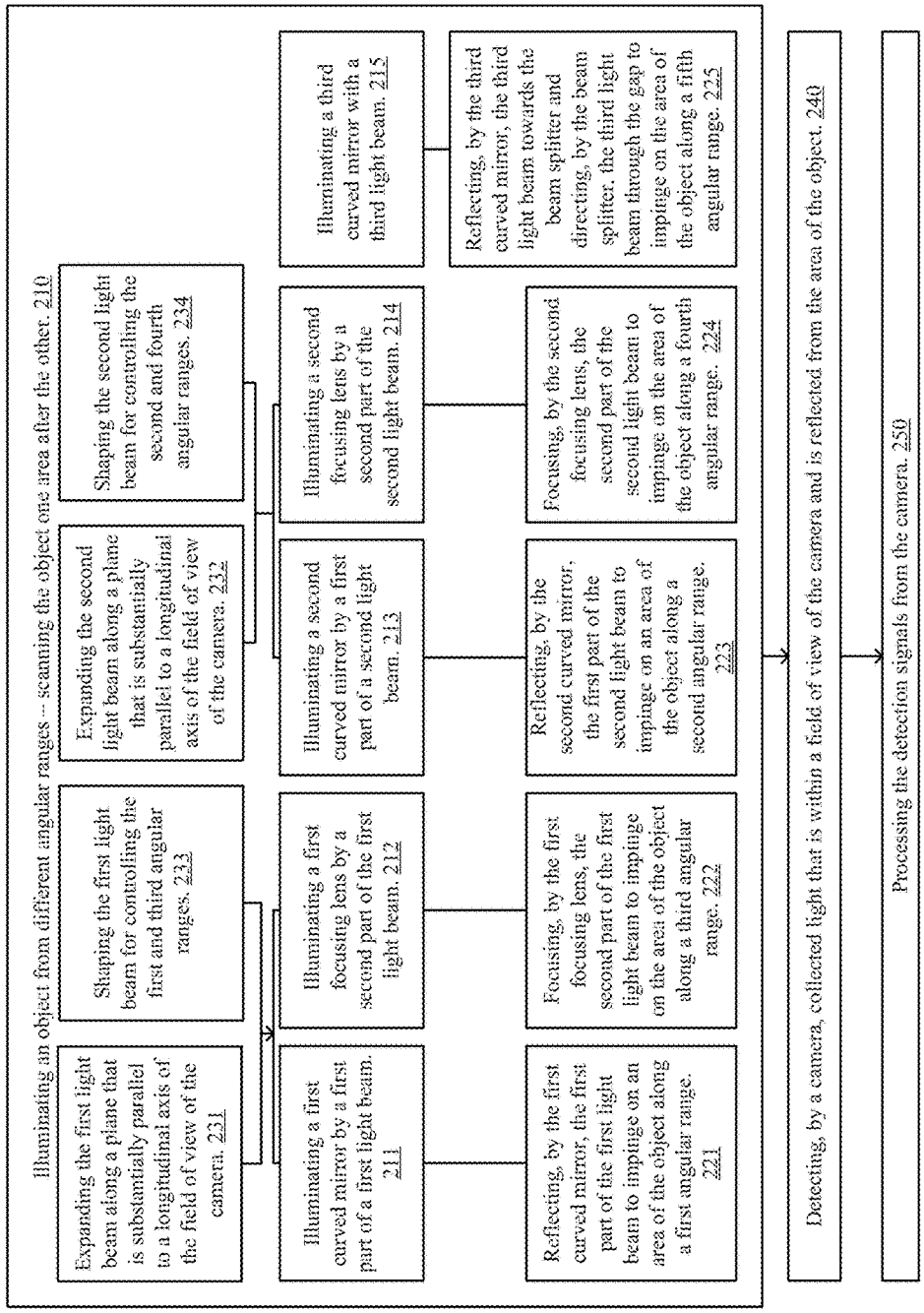
FIG. 7 illustrates a method according to an embodiment of the invention.

FIG. 7 illustrates method 200 according to an embodiment of the invention.

Method 200 may start by step 210 of illuminating an object from different angular ranges—scanning the object one area after the other.

Step 210 may include repeating, for different areas of the object the steps of:
a. Illuminating (211) a first curved mirror by a first part of a first light beam.
b. Illuminating (212) a first focusing lens by a second part of the first light beam.
c. Illuminating (213) a second curved mirror by a first part of a second light beam.
d. Illuminating (214) a second focusing lens by a second part of the second light beam.
e. Reflecting (221), by the first curved mirror, the first part of the first light beam to impinge on an area of the object along a first angular range.
f. Focusing (222), by the first focusing lens, the second part of the first light beam to impinge on the area of the object along a third angular range.
g. Reflecting (223), by the second curved mirror, the first part of the second light beam to impinge on an area of the object along a second angular range. and
h. Focusing (224), by the second focusing lens, the second part of the second light beam to impinge on the area of the object along a fourth angular range.

The first angular range, the second angular range, the third angular range and the fourth angular range differ from each other.

Steps 221, 222, 223 and 224 follow steps 211, 212, 213 and 214, respectively.

Step 210 may be followed by step 240 of detecting, by a camera, collected light that is within a field of view of the camera and is reflected from the area of the object.

The area of the object may have an elongated shape and may be parallel to the field of view of the camera.

Step 240 may be followed by step 250 of processing the detection signals from the camera. The processing may be executed by an image processor and may be executed during an inspection of the object.

Step 210 may include step 231 of expanding the first light beam along a plane that is substantially parallel to a longitudinal axis of the field of view of the camera.

Step 210 may include step 232 of expanding the second light beam along a plane that is substantially parallel to a longitudinal axis of the field of view of the camera.

Step 210 may include step 233 of shaping the first light beam for controlling the first and third angular ranges.

Step 210 may include step 234 of shaping the first light beam for controlling the first and third angular ranges.

Steps 231 and 232 may precede steps 211 and 212.

Steps 233 and 234 may precede steps 213 and 214.

There may be no angular gap between the first angular range and the third angular range. Although that such a gap may exist.

There may be no angular gap between the second angular range and the fourth angular range. Although that such a gap may exist.

The camera has an optical axis. The first and third angular ranges may be positioned at one side of the optical axis and the second and fourth angular ranges may be positioned at another side of the optical axis.

There may be a gap between the first curved mirror and the second curved mirror. The collected light (of step 240) may pass through the gap.

Step 210 may include step 215 of illuminating a third curved mirror with a third light beam and step 225 of reflecting, by the third curved mirror, the third light beam towards the beam splitter and directing, by the beam splitter, the third light beam through the gap to impinge on the area of the object along a fifth angular range.

Method 200 may be executed by system 100 of FIG. 1.

There may be provided a method for inspecting an inspected article using a system as illustrated above. The method may include illuminating the sample using the system of FIG. 1, collecting light from the object and generating detection signals.

Furthermore, those skilled in the art will recognize that boundaries between the functionality of the above described operations are merely illustrative. The functionality of multiple operations may be combined into a single operation, and/or the functionality of a single operation may be distributed in additional operations. Moreover, alternative embodiments may include multiple instances of a particular operation, and the order of operations may be altered in various other embodiments.

Thus, it is to be understood that the architectures depicted herein are merely exemplary, and that in fact many other architectures can be implemented which achieve the same functionality. In an abstract, but still definite sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

However, other modifications, variations, and alternatives are also possible. The specifications and drawings are, accordingly, to be regarded in an illustrative rather than in a restrictive sense.

The word "comprising" does not exclude the presence of other elements or steps then those listed in a claim. It is understood that the terms so used are interchangeable under appropriate circumstances such that the embodiments of the invention described herein are, for example, capable of operation in other orientations than those illustrated or otherwise described herein.

Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe.

Thus, these terms are not necessarily intended to indicate temporal or other prioritization of such elements. The mere fact that certain measures are recited in mutually different claims does not indicate that a combination of these measures cannot be used to advantage.

We claim:

1. An inspection system having an expanded angular coverage, the inspection system comprise:
    a line camera;
    a first curved mirror;
    a second curved mirror;
    a first focusing lens that is positioned between the first mirror and an object;
    a second focusing lens that is positioned between the second mirror and the object;
    a first light source that is configured to direct a first part of a first light beam towards the first curved mirror and a second part of the first light beam towards the first focusing lens;
    a second light source that is configured to direct a first part of a second light beam towards the second curved mirror and a second part of the second light beam towards the second focusing lens;
    wherein the first curved mirror is configured to reflect the first part of the first light beam to impinge on an area of the object along a first angular range;
    wherein the second curved mirror is configured to reflect the first part of the second light beam to impinge on the area of the object along a second angular range;
    wherein the first focusing lens is configured to focus the second part of the first light beam to impinge on the area of the object along a third angular range;
    wherein the second focusing lens is configured to focus the second part of the second light beam to impinge on the area of the object along a fourth angular range;
    wherein the first angular range, the second angular range, the third angular range and the fourth angular range differ from each other; and
    wherein the camera is configured to detect collected light that is within a field of view of the camera and is reflected from the area of the object.

2. The inspection system according to claim 1, wherein the area of the object has an elongated shape and is parallel to the field of view of the camera.

3. The inspection system according to claim 1, wherein the first light source is followed by a first beam expander for expanding the first light beam along a plane that is substantially parallel to a longitudinal axis of the field of view of the camera.

4. The inspection system according to claim 1, wherein the first light source is followed by a first beam shaper for controlling the first and third angular ranges.

5. The inspection system according to claim 1, wherein there is no angular gap between the first angular range and the third angular range.

6. The inspection system according to claim 1, wherein there is no angular gap between the second angular range and the fourth angular range.

7. The inspection system according to claim 1, wherein the camera has an optical axis; wherein the first and third angular ranges are positioned at one side of the optical axis and wherein the second and fourth angular ranges are positioned at another side of the optical axis.

8. The inspection system according to claim 1, wherein there is a gap between the first curved mirror and the second curved mirror; and wherein the camera is configured to detect light that passes through the gap.

9. The inspection system according to claim 8, comprising a third curved mirror, a beam splitter and a third light source; wherein the third light source is configured to direct a third light beam towards the third curved mirror; wherein the third curved mirror is configured to reflect the third light beam towards the beam splitter; wherein the beam splitter is configured to direct the third light beam through the gap and towards the area of the object along a fifth angular range.

10. The inspection system according to claim 1, wherein the first and second curved mirrors are elliptical or spherical mirrors; wherein the first and second focusing mirrors are Fresnel mirrors or cylindrical mirrors; and wherein the first and second light sources are dark field light sources.

11. A method for inspecting an object, the method comprises:
    illuminating a first curved mirror by a first part of a first light beam;
    illuminating a first focusing lens by a second part of the first light beam;
    illuminating a second curved mirror by a first part of a second light beam;
    illuminating a second focusing lens by a second part of the second light beam;
    reflecting, by the first curved mirror, the first part of the first light beam to impinge on an area of the object along a first angular range;
    reflecting, by the second curved mirror, the first part of the second light beam to impinge on an area of the object along a second angular range;
    focusing, by the first focusing lens, the second part of the first light beam to impinge on the area of the object along a third angular range;
    focusing, by the second focusing lens, the second part of the second light beam to impinge on the area of the object along a fourth angular range;
    wherein the first angular range, the second angular range, the third angular range and the fourth angular range differ from each other; and
    detecting, by a camera, collected light that is within a field of view of the camera and is reflected from the area of the object.

12. The method according to claim 11, wherein the area of the object has an elongated shape and is parallel to the field of view of the camera.

13. The method according to claim 11, comprising expanding the first light beam along a plane that is substantially parallel to a longitudinal axis of the field of view of the camera.

14. The method according to claim 11, comprising shaping the first light beam for controlling the first and third angular ranges.

15. The method according to claim 11, wherein there is no angular gap between the first angular range and the third angular range.

16. The method according to claim 11, wherein there is no angular gap between the second angular range and the fourth angular range.

17. The method according to claim 11, wherein the camera has an optical axis; wherein the first and third angular ranges are positioned at one side of the optical axis and wherein the second and fourth angular ranges are positioned at another side of the optical axis.

18. The method according to claim 11, wherein there is a gap between the first curved mirror and the second curved mirror; and wherein the collected light passes through the gap.

19. The method according to claim 18, comprising illuminating a third curved mirror with a third light beam; reflecting, by the third curved mirror, the third light beam towards the beam splitter; directing, by the beam splitter, the third light beam through the gap to impinge on the area of the object along a fifth angular range.

20. The method according to claim 11, wherein the first and second curved mirrors are elliptical or spherical mirrors; wherein the first and second focusing mirrors are Fresnel mirrors or cylindrical mirrors; and wherein the first and second light sources are dark field light sources.

* * * * *